(12) United States Patent
De Wit et al.

(10) Patent No.: US 8,016,737 B2
(45) Date of Patent: Sep. 13, 2011

(54) METHOD FOR REMOVING A FLUID FROM A CONTAINER AND DEVICE THEREFOR

(75) Inventors: Jacobus Petrus Cornelis De Wit, Oudenbosch (NL); Robert Helene Ghislain Dirks, Oudenbosch (NL); Edwin Van Zon, Roosendaal (NL); Leendert Jacobus Woudenberg, Vlaardingen (NL)

(73) Assignee: Rijk Zwaan Zaadteelt en Zaadhandel B.V., de Lier (NL)

( * ) Notice: Subject to any disclaimer, the term of this patent is extended or adjusted under 35 U.S.C. 154(b) by 491 days.

(21) Appl. No.: 12/152,584

(22) Filed: May 14, 2008

(65) Prior Publication Data
US 2008/0296230 A1    Dec. 4, 2008

Related U.S. Application Data

(63) Continuation-in-part of application No. PCT/NL2006/000566, filed on Nov. 13, 2006.

(30) Foreign Application Priority Data

Nov. 14, 2005   (NL) ...................................... 1030409

(51) Int. Cl.
*B01D 21/26*   (2006.01)

(52) U.S. Cl. ............................................. 494/37; 494/16
(58) Field of Classification Search .................. 494/13, 494/14, 16, 20, 21, 37
See application file for complete search history.

(56) References Cited

U.S. PATENT DOCUMENTS

| 3,849,072 A | 11/1974 | Ayres |
| 2002/0047003 A1 | 4/2002 | Bedingham |
| 2002/0104808 A1* | 8/2002 | Blasetti et al. .................. 494/16 |
| 2005/0069913 A1 | 3/2005 | Mian |

FOREIGN PATENT DOCUMENTS

| WO | WO 96/07097 | 3/1996 |
| WO | WO 97/21090 | 6/1997 |
| WO | WO 03/054509 | 7/2003 |

* cited by examiner

*Primary Examiner* — Walter D Griffin
*Assistant Examiner* — Timothy Cleveland
(74) *Attorney, Agent, or Firm* — Vedder Price P.C.; Thomas J. Kowalski; Deborah L. Lu

(57) ABSTRACT

Provided is a method for removing a liquid, in particular a supernatant, from a container with a sample, by creating an opening in a container with a sample consisting of solid constituents and a liquid, and subsequently centrifuging the container so as to cause the liquid to flow out of the container through the created opening. Also provided is a device for making a container suitable for use in the method.

9 Claims, 4 Drawing Sheets

METHOD FOR REMOVING A FLUID FROM A CONTAINER AND DEVICE THEREFOR

CROSS-REFERENCE TO RELATED APPLICATIONS

This application is a continuation-in-part of International application no. PCT/NL2006/000566, filed on Nov. 13, 2006, published as WO 2007/055573 on May 18, 2007, and claiming priority to Netherlands application no. 1030409, filed on Nov. 14, 2005.

The foregoing applications and all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturers' instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a method for removing a liquid from a container in simple manner. The invention further relates to a device for making a container suitable for use thereof in the method.

BACKGROUND OF THE INVENTION

A plurality of centrifuging steps are often performed in many microbiological and molecular-biological procedures, such as for instance DNA isolation. A container with a sample therein is centrifuged here in order to separate the solid constituents (referred to as pellet or debris) from the liquid (the supernatant). After the centrifugation the supernatant is removed from each container with sample. Because there are often tens of samples or more, this is very labour-intensive and requires a great deal of attention and, in addition, expensive plastic disposable materials such as pipette tips.

SUMMARY OF THE INVENTION

It is an object of the invention to provide a method for removing a liquid, in particular a supernatant, more easily from a tube. It is a further object of the invention to provide a device with which containers can be adapted such that they become suitable for use in this method.

BRIEF DESCRIPTION OF THE DRAWINGS

The invention is further illustrated in the accompanying figures.

The laser used comes for instance from the company Synrad Inc., Mukilteo, Wash., USA, and is of the type Synrad 25W Marking laser FSV25SFB with smart marking head; 110×100 field size (FH30-200).

The tubes and holders which can be used in the shown machine come for instance from the company Matrix Technologies Corp., Hudson, N.H., USA. The deep well tubes are for instance tubes as per catalogue item 4430. The holder is for instance a Snaprack (catalogue item 4893).

Figure 1D:
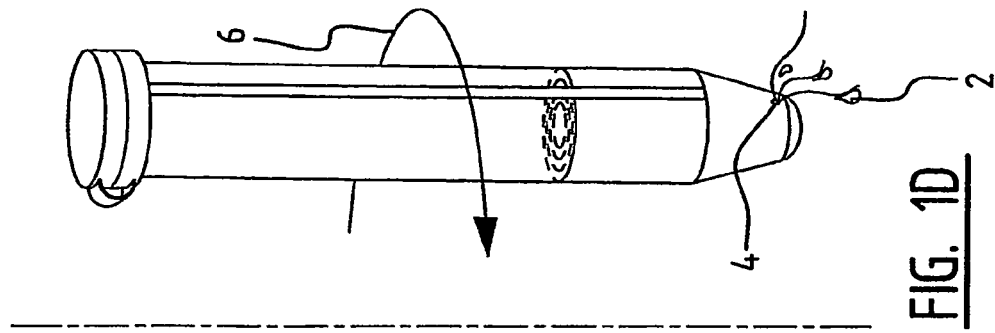
FIG. 1 shows the principle of the invention.
FIG. 1A shows an inverted container (1) with liquid (2). An opening (4) is then arranged some distance from bottom (3) by means of a laser beam (5) (FIG. 1B). The container is then turned over (FIG. 1C) and placed in a centrifuge indicated schematically with arrow (6), whereby the liquid (2) in the tube flows out through opening (4) (FIG. 1D).
Figure 1C:
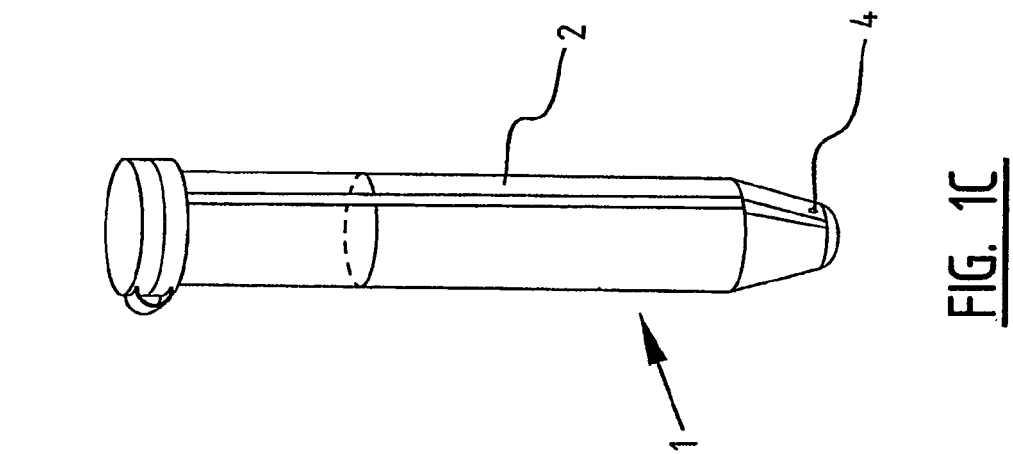
Figure 1B:
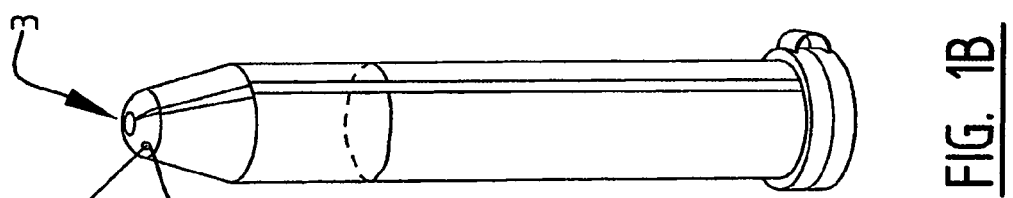
Figure 1A:
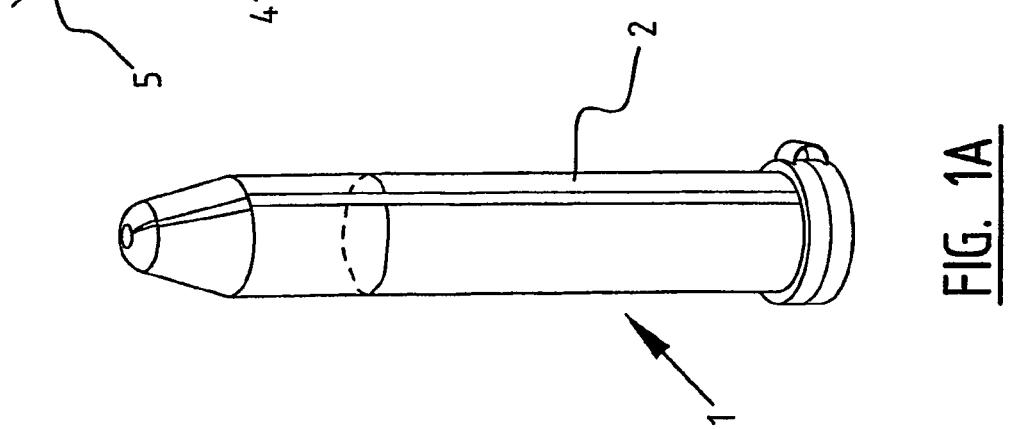
Figure 2:
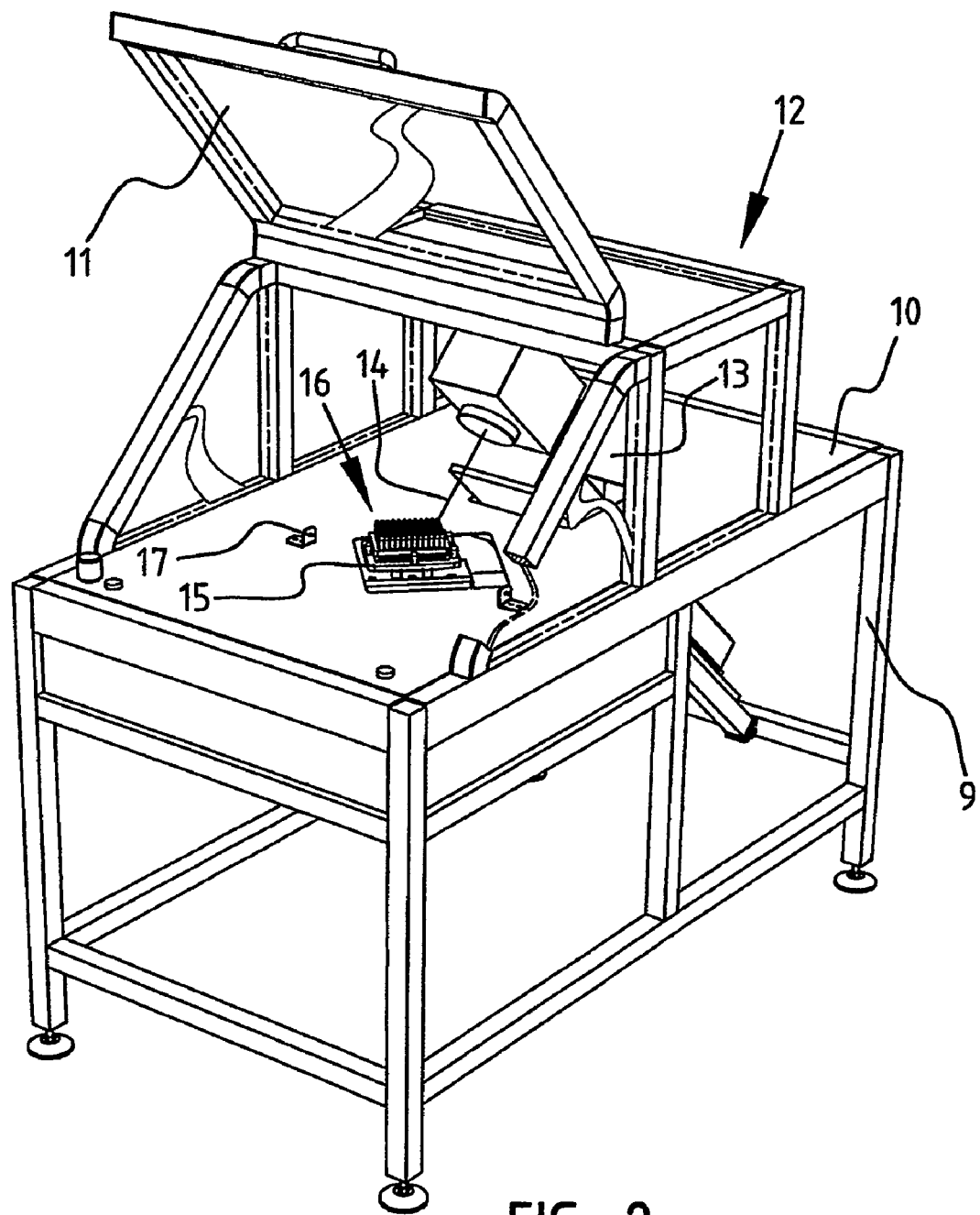
FIG. 2 shows a perspective view of a device according to the invention. Placed on a frame (9) is a tabletop (10), on which is provided a protective housing (12) equipped with an access cover (11). Situated in the housing is laser device (13) which produces a laser beam (14). A rack (15) for the containers (16) to be perforated is placed in the path of laser beam (14). The position of rack (15) with containers (16) is monitored by photocells (17).
Figure 3:
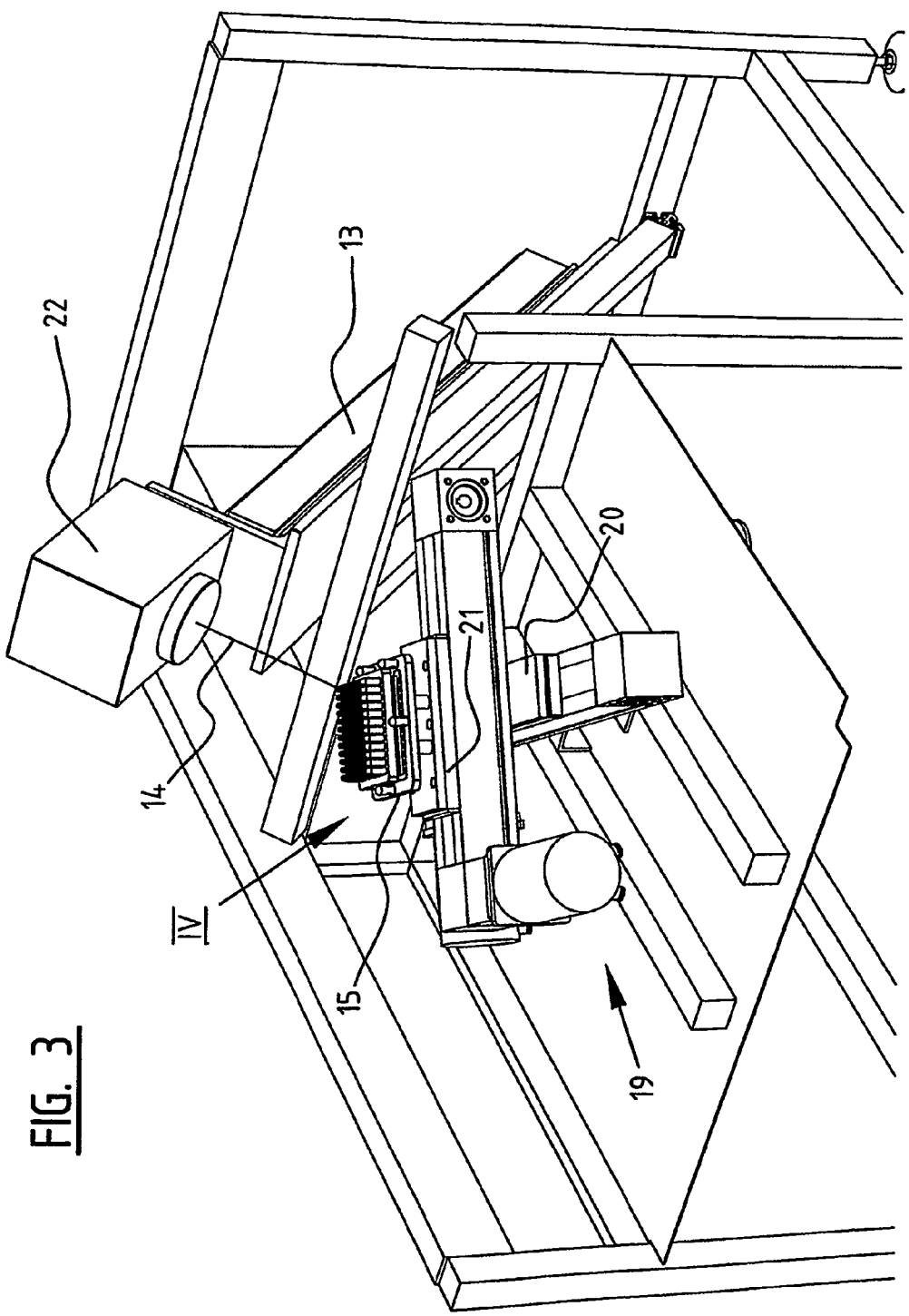

FIG. 3 shows a detail view of the device of FIG. 2. FIG. 3 shows the positioning of rack (15) by means of a positioning device (19) consisting of two carriages (20) and (21) movable relative to each other. Carriage (20) can be moved in X-direction and carriage (21) in Y-direction. As can be seen in FIG. 2, positioning device (19) is situated during use under tabletop (10) which is provided with a recess (18) through which the rack (15) with containers (16) protrudes. Laser device (13) produces a laser beam (14) which via mirror unit (22) is incident upon the container and there arranges an opening.

In order to arrange the openings at the correct location a precise positioning of the containers is desired.

Figure 4:
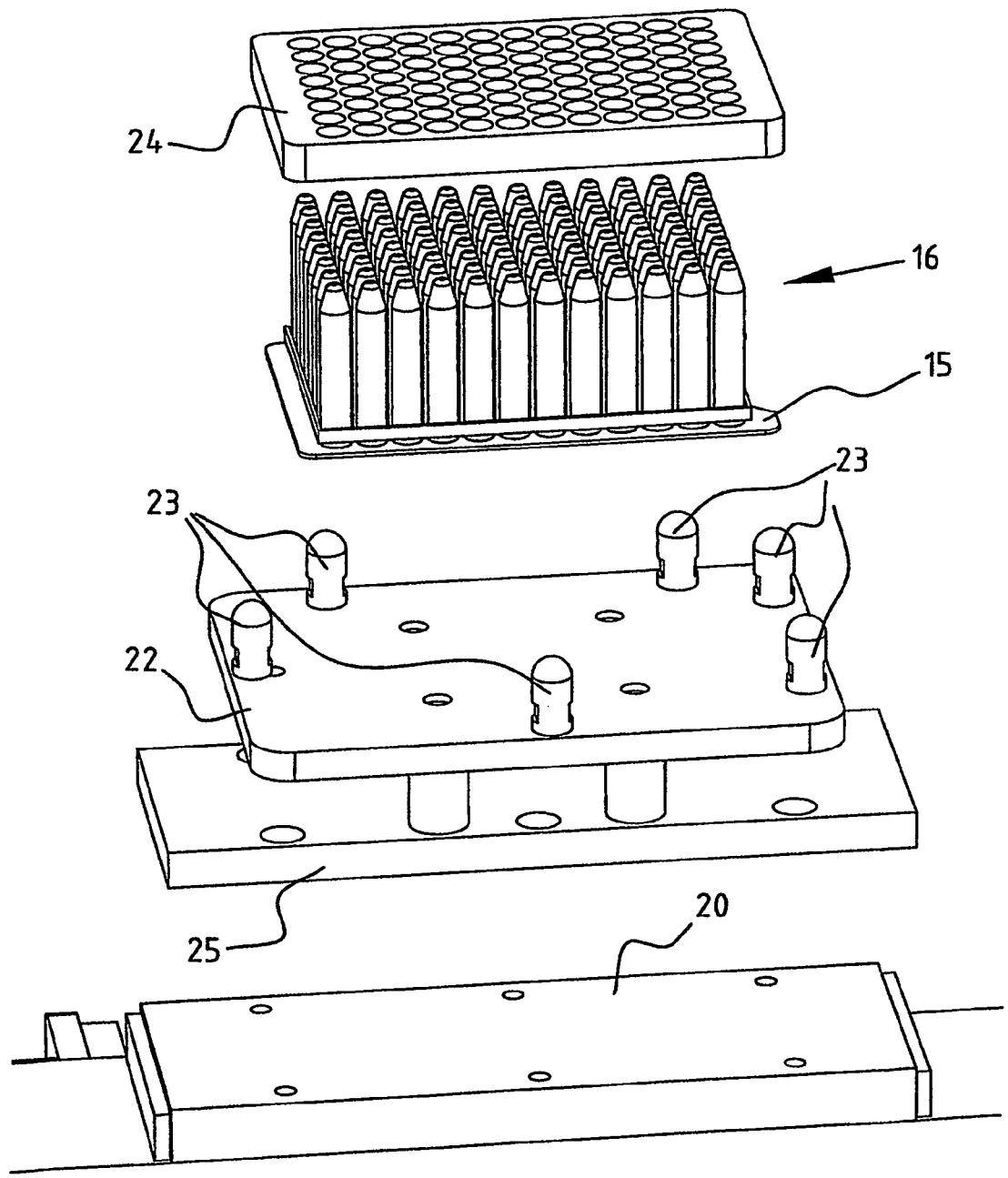

FIG. 4 shows a perspective view with exploded parts of the holder for the containers to be perforated. FIG. 4 shows rack (15) for the containers (16) to be perforated, with a part of positioning device (19). Rack (15), in which the tubes are placed upside down, is fixed onto a platform (22). Situated on platform (22) are centring pins (23) which ensure that the rack is positioned correctly relative to the laser device. The containers themselves are held in the correct position by a spacer block (24) which is provided with recesses for receiving the containers. Platform (22) is mounted on one of the carriages (20) of positioning device (19) via a filler block (25).

DETAILED DESCRIPTION

The first object is achieved by the invention with a method comprising of providing a container with a sample consisting of solid constituents and a liquid, creating an opening in the container, and subsequently centrifuging the container so as to cause the liquid to flow out of the container.

The opening is preferably made at a determined distance from the bottom of the container prior to the centrifuging step. The container is then centrifuged and the liquid will flow out of the tube through the arranged opening during the centrifugation, while the pellet remains behind. Owing to the invention, overpipetting of the supernatant becomes unnecessary, whereby a pipetting step is no longer required.

The position of the opening at some distance from the bottom of the container ensures that the solid substances remain in the container and only the liquid flows out. This furthermore prevents blockage of the opening by solid constituents from the solution, such as cell constituents or magnetic spheres. The position of the opening is preferably in the lower half of the container, and is preferably chosen to be sufficiently close to the bottom to allow substantially all liquid to flow out. The opening is however preferably not made in the bottom.

Creating an opening in the container can take place in various ways, such as by means of piercing, burning, a water jet, drilling, etc. In a particularly advantageous embodiment use is however made of a laser.

Different techniques can be applied to prevent the liquid flowing out immediately during creating of the opening. The containers can for instance be reversed so that the bottom is at the top and is not in contact with the liquid. The liquid can also be temporarily immobilized, for instance by freezing or by gelling of the liquid. The latter can, for instance, take place using calcium alginate. The gelling is reversed by removing the calcium ions using sodium citrate or sodium phosphate, whereafter the liquid can be removed by centrifugation. See also herefor O. Smidsrød, G. Skjåk-Bræk. 1990. Alginate as immobilization matrix for cells. Tibtech—Vol. 8, March 1990, 71-78.

One or more openings can be created per container.

A device according to the invention comprises perforating means for creating an opening in a container with a sample consisting of solid constituents and a liquid. A holder for the containers to be perforated can further be present inside the device, although such a holder can also be provided separately.

In addition, positioning means are preferably provided in advantageous manner with which the container for perforating is brought into contact with the perforating means. The perforating means can be formed by any device with which an opening can be arranged in the container. Examples are a drill, a piercing device, a water jet, a heating element, a laser and the like. A plurality of perforating means can be placed mutually adjacently in order to make a plurality of openings simultaneously. Use can thus be made for instance of a kind of bed of nails on which the perforating means are at the same distance from each other as the containers for perforating in their rack. With one movement the perforating means, in particular piercing means, can then be pressed simultaneously through a plurality of tubes.

According to a preferred embodiment of the invention, the opening is arranged by means of a laser. The advantage hereof is that the arranged opening is simultaneously heated. Nor is physical contact made with the tubes. Cross-contamination is thereby prevented.

The invention is suitable for all containers from which the liquid must be removed while the solid constituents must remain behind. The invention is particularly suitable for containers which are used in laboratories, such as microtiter plates, reaction tubes which are also known as Eppendorf tubes, deep well tubes, test tubes, etc. The containers can be manufactured from various materials such as plastic or glass.

In a specific embodiment the invention comprises of perforating so-called deep well tubes at a determined height with a laser. Such containers are much used in, for instance, microbiological and molecular-biological work.

The perforation is, for instance, made several mm above the bottom. The debris comes to lie at the bottom of the tube and the opening must be above this. After making the hole with the laser the deep well tubes are placed in a centrifuge, whereafter the supernatant enters the surrounding deep well rack during the centrifugation.

The device shown in the figures is only one embodiment of the device according to the invention. Many variations of the same principle are possible, and all form part of the invention.

We claim:

1. A method for removing a supernatant from a container, the method comprising the consecutive steps of:
   (a) providing a container containing a sample comprising:
       solid constituents; and
       a supernatant;
   (b) creating an opening in the container; and
   (c) centrifuging the container such that the supernatant flows out of the container through the opening.

2. The method of claim 1, wherein the container comprises an upper half and a lower half and wherein the opening is created in the lower half.

3. The method of claim 1, wherein the opening is created by means selected from the group consisting of piercing, burning, drilling, water jet, and laser.

4. The method of claim 1, further comprising turning the container upside down prior to creating the opening.

5. The method of claim 1, wherein the supernatant is immobilized prior to creating the opening, and wherein immobilization is reversed prior to centrifuging.

6. The method of claim 5, wherein the supernatant is immobilized by freezing and immobilization is reversed by heating.

7. The method of claim 5, wherein the supernatant is immobilized by gelling.

8. The method of claim 7, wherein the gelling is realized using calcium alginate, and wherein the gelling is reversed by removing calcium ions.

9. The method of claim 8, wherein calcium ions are removed with sodium citrate or sodium phosphate.

* * * * *